United States Patent [19]
Akiyama et al.

[11] 3,943,751
[45] Mar. 16, 1976

[54] METHOD AND APPARATUS FOR CONTINUOUSLY MEASURING HYDROGEN CONCENTRATION IN ARGON GAS

[75] Inventors: Takao Akiyama; Satoru Takani; Hideo Atsumo, all of Mito, Japan

[73] Assignee: Doryokuro Kakunenryo Kaihatsu Jigyodan, Tokyo, Japan

[22] Filed: Apr. 22, 1975

[21] Appl. No.: 570,374

[30] Foreign Application Priority Data
May 8, 1974 Japan.................... 49-50931

[52] U.S. Cl................................. 73/27 R
[51] Int. Cl.².................................. G01N 31/00
[58] Field of Search............. 73/19, 23, 26, 27 R

[56] References Cited
UNITED STATES PATENTS

| | | | |
|---|---|---|---|
| 3,146,223 | 8/1964 | Cheney............................. | 73/26 X |
| 3,731,523 | 5/1973 | Vissers et al...................... | 73/19 |
| 3,769,837 | 11/1973 | Kraus et al........................ | 73/23 |
| 3,803,900 | 4/1974 | Maillard........................... | 73/23 |

OTHER PUBLICATIONS
2,526,038 10001950 Nelson 73 23

Takahashi, "Determination of Hydrogen in Sodium by Amalgamation Method," *J. Nucl. Sci. Technol.*, Vol. 10, No. 1, (Jan. 1973), pp. 54–60.

Vissers et al., "A Hydrogen Monitor for Detection of Leaks in LMFBR Steam Generators," *Nuclear Technology*, Vol. 12, (Oct. 71), pp. 218–225.

*Primary Examiner*—Charles A. Ruehl
*Attorney, Agent, or Firm*—Wenderoth, Lind & Ponack

[57] ABSTRACT

A method and an apparatus for continuously measuring the hydrogen concentration in argon gas containing hydrogen and other impurities. The argon gas containing impurities is continuously passed through a high temperature metal getter to thereby remove impurities other than hydrogen from the argon gas and produce a two-component mixture of gases consisting of argon and hydrogen. The two-component gas is then continuously introduced to a thermal conductivity detector and the hydrogen concentration can be determined from the detected thermal conductivity.

11 Claims, 5 Drawing Figures

METHOD AND APPARATUS FOR CONTINUOUSLY MEASURING HYDROGEN CONCENTRATION IN ARGON GAS

BACKGROUND OF THE INVENTION

This invention relates generally to detecting water leaks in a steam generator used in a nuclear reactor containing liquid sodium coolant, and more particularly to a method and an apparatus for continuously measuring concentrations of hydrogen in the cover gas, i.e., argon gas, used in a nuclear reactor.

In the steam generator used in a nuclear reactor containing liquid sodium coolant, water is heated by high temperature liquid sodium to generate steam. When a water leak occurs in a pipe wall which separates liquid sodium from water, a violent reaction takes place between water and liquid sodium and this can result in failure or damage of the steam generator. Hydrogen gas is produced in the course of the reaction, and is then transferred to the argon gas phase with which the space above the free surface of the liquid sodium is filled. Therefore, it is possible to detect water leaks in the steam generator system by continuously monitoring the hydrogen concentration in the argon cover gas.

In order to minimize damage to the steam generator system and to maintain a safe operation of the system, rapid and sensitive detection of hydrogen in the argon cover gas is important.

Prior methods of detecting the hydrogen concentration in argon gas include gas chromatograhy and a method using a metal membrane. In the gas chromatograph method, as shown in FIG. 1, a sample 1 of gas is auotmatically and intermittently picked up from the argon cover gas by a sampler 2, and the sample gas is introduced together with a carrier gas 3 into a column 4 to separate hydrogen from the argon cover gas. Then, the separated and eluted hydrogen and carrier gas are respectively subjected to a measurement of their thermal conductivities by two thermal conductivity cells 5, and the concentration of hydrogen in the argon can be read from the difference between these two thermal conductivity values, and can be recorded by a recorder 7. The column 4 and thermal conductivity cells 5 are contained in an oven 6.

To make the measurement by this system rapid, the system has been designed to make the retention time of the hydrogen as short as possible, on the assumption that no impurity gases other than hydrogen exist in the sample gas, so as to measure hydrogen concentrations at time intervals of about three minutes. This system, therefore, has the following disadvantages:

1. If there are impurity gases, other than hydrogen in the sample gas, mainly gases such as oxygen and nitrogen, they are simultaneously eluted with the hydrogen since they cannot be completely separated from hydrogen. This leads to a positive error in the numerical indication of hydrogen concentration.

2. In order to completely separate impurity gases from hydrogen, it is necessary to measure hydrogen concentrations at time intervals of more than five minutes. Therefore, this system is useless for quickly detecting the occurrence of gases produced as a result of the reaction between water and liquid sodium, i.e., occurrence of water leaks.

3. Measurement of hydrogen concentrations according to this system is made intermittently, not continuously.

4. The apparatus used in this system is so large and complicated that the places where it can be installed are limited and the cost of the apparatus is high.

The prior method using a metal membrane utilizes the characteristic that hydrogen can selectively permeate and diffuse through a membrane of nickel or palladium. One apparatus which is often used in this method is shown in FIG. 2. The membrane tube 11 is positioned within a chamber 13 in an electric furnace 12 and the tube 11 and chamber 13 are maintained at a temperature of 450° to 500°C. On the other hand, the insides of both the membrane tube 11 and a hydrogen gas detector 14 (e.g., an ionization gauge) are kept at a high vacuum by means of a vacuum pump 15 and diffusion pump 16. An orifice 17 is interposed between the exhaust side of the membrane tube 11 and the detector 14, in order to maintain the inside of the vacuum system at a constant vacuum. When argon gas containing hydrogen is introduced into the chamber 13, only hydrogen permeates through the membrane and enters through the inside of the tube 11 into the detector 14, where the hydrogen concentration is continuously detected as a change of degree of vacuum.

This prior method, however, has the following disadvantages:

1. In order to increase the permeation of hydrogen through the metal membrane, the thickness of the metal membrane is reduced as much as possible, for example until it has a thickness of 50 to 100 $\mu$. Therefore, the metal membrane is easily cracked, deformed and burst under thermal stress.

2. It is assumed in this method that only hydrogen can selectively permeate through the metal membrane and that the changes of the degree of vacuum in the hydrogen detector are produced only by hydrogen contained in the sample gas. However, when microscopic cracks have been produced in the metal membrane, a very small amount of argon can also permeate through the cracks and enter the hydrogen detector. In addition, the sensitivity of the ionization gauge is increased as the mass number of the gas which is in contact with the gauge becomes larger. For these reasons, there is a possibility that noticeable errors can occur in the indication of the hydrogen concentration.

3. If the sample gas contains hydrocarbon gases and/or sodium vapors, they attach to the surface of the metal membrane and cause a decrease of the permeation of hydrogen through the membrane. Furthermore, they cause the surface of the membrane to burst due to the cementation thereof.

4. It is impossible to foresee the deterioration of the metal membrane and the production of the microscopic cracks therein.

OBJECTS AND BRIEF SUMMARY OF THE INVENTION

Therefore, it is an object of this invention to provide a method and apparatus to carry out satisfactory and accurate measurement of hydrogen concentration in argon gas, although impurities other than hydrogen exist in the argon gas.

It is another object of this invention to provide a method and apparatus for promptly and continuously measuring a very small amount of hydrogen contained in argon gas, to thereby detect water leaks in a steam generator system used in a nuclear reactor.

It is a further object of this invention to provide a reliable apparatus for promptly and continuously measuring hydrogen concentrations in argon gas, which is easily designed and is compact.

In accordance with the method of the present invention, argon gas containing hydrogen and other impurities is continuously passed through a high temperature metal getter, thereby removing impurities other than hydrogen from the argon gas and producing two-component mixture of gases consisting only of argon and hydrogen. The two-component mixture of gases thus produced is then introduced into a detector in which the thermal conductivity of the gas is continuously detected. The hydrogen concentration can be determined from the detected value of the thermal conductivity.

Other objects and advantages of the present invention will become apparent upon reading the following description and upon reference to the accompanying drawings.

DETAILED DESCRIPTION OF THE INVENTION

The apparatus according to the present invention comprises an impurity-removing means composed of a high temperature metal getter through which the argon gas is passed, and a thermal conductivity detector wherein the thermal conductivity of the gas passed through the impurity-removing means is detected. The hydrogen concentration in the gas can be measured from the thermal conductivity thus detected.

The impurity-removing means comprises a column in which the metal getter is packed and through which the gas is passed, and means for heating the metal getter up to the desired temperature and maintaining the temperature of the getter.

It has been generally considered that impurities in argon cover gas are hydrogen, oxygen, nitrogen, carbon monoxide, carbon dioxide, hydrocarbons, and the like.

In order to remove impurities other than hydrogen from the argon gas prior to a determination of the hydrogen concentration therein, a high temperature metal getter having poor reactivity with hydrogen but having a high reactivity with impurities other than hydrogen is used according to this invention. A metal getter useful in this invention is a getter made from a metal taken from the group consisting of titanium, zirconium, niobium and the like. It has been previously known that these metal getters react with hydrogen at a temperature of 200° to 600°C to form hydrides and react with oxygen, nitrogen or carbonic compounds at a temperature of 700° to 1100°C to form oxides, nitrides or carbides.

Figure 1:
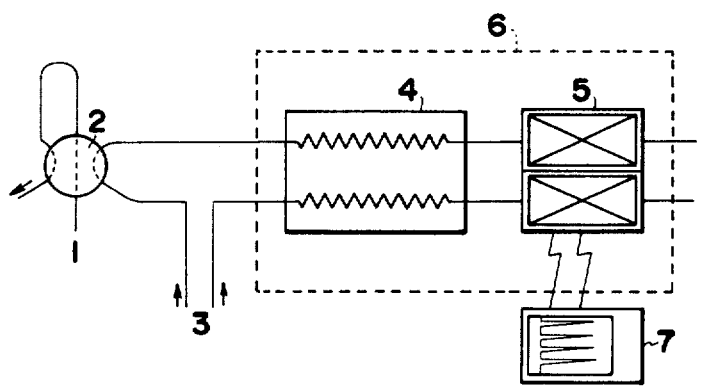
FIG. 1 is a diagrammatic representation of a gas chromatography process used in the prior art.
Figure 2:
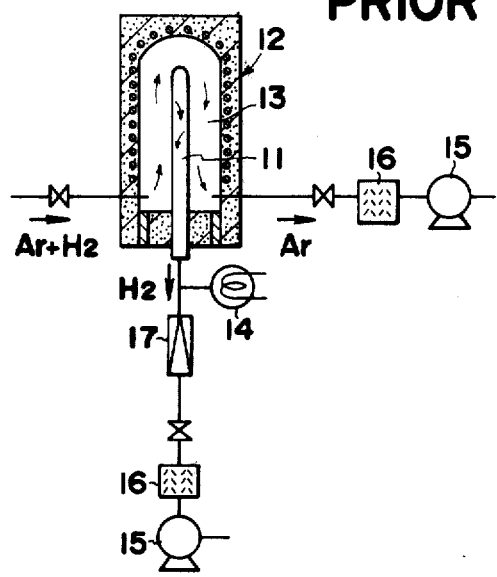
FIG. 2 is a diagrammatic representation of a prior art method using a metal membrane.
Figure 3:
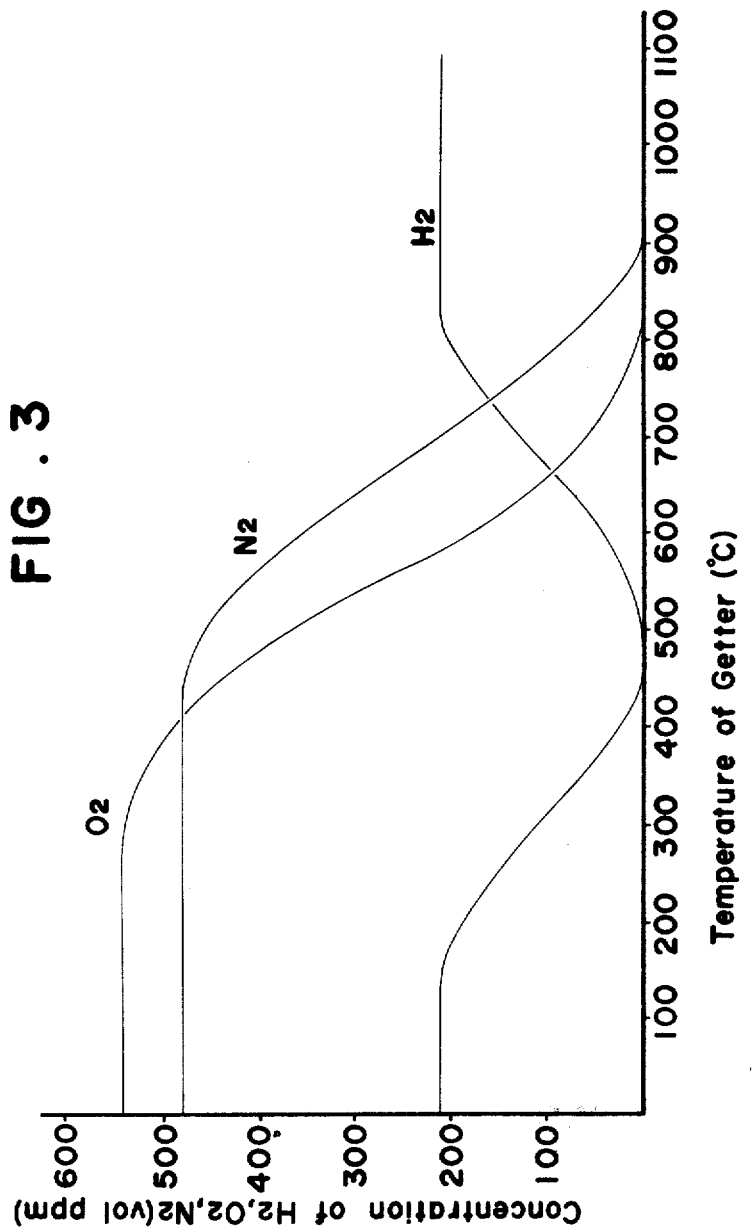
FIG. 3 is a graph illustrating the relation between the temperatures of a getter and the concentrations of hydrogen, oxygen and nitrogen gases in argon gas.

An experiment to demonstrate the action of the metal getter was conducted by passing sample argon gas containing impurities through a spongy titanium getter, gradually elevating the temperature of the getter from 20° to 1100°C, and determining the impurity concentrations in the prepared sample gas. The result obtained is shown by the graph in FIG. 3. As is apparent from the graph, hydrogen reacts at 200° to 750°C, while scarcely any reaction takes place above 800°C. Oxygen and nitrogen begin to react at 300°C and 500°C, respectively, and completely react above 800°C and 900°C, respectively, so as to be completely removed from the sample argon gas. It will therefore be understood that when the temperature of the getter is maintained above about 900°C, then the hydrogen in the argon gas will not react with the getter, while oxygen and nitrogen are completely removed from argon gas. It is obviously supposed that carbon monoxide and dioxide also react with the getter above about 900°C so as to be removed from the sample argon gas.

Thus, by continuously passing the sample argon gas containing hydrogen and other impurities through the high temperature metal getter, a two-component mixture of gas consisting of only argon and hydrogen can be produced.

The thermal conductivity of the thus produced two-component gas mixture is greatly changed due to the hydrogen content of the gas mixture, since there is a large difference between the thermal conductivity of argon and that of hydrogen. Namely, argon gas has a thermal conductivity of 3.88 cal/sec.cm.deg. at 0°C., while hydrogen gas has 41.84 cal/sec.cm.deg. at 0°C. Therefore, the hydrogen concentration can be continuously determined by directly introducing the two-component gas mixture into a thermal conductivity detector of the hot-wire bridge type.

Figure 4:
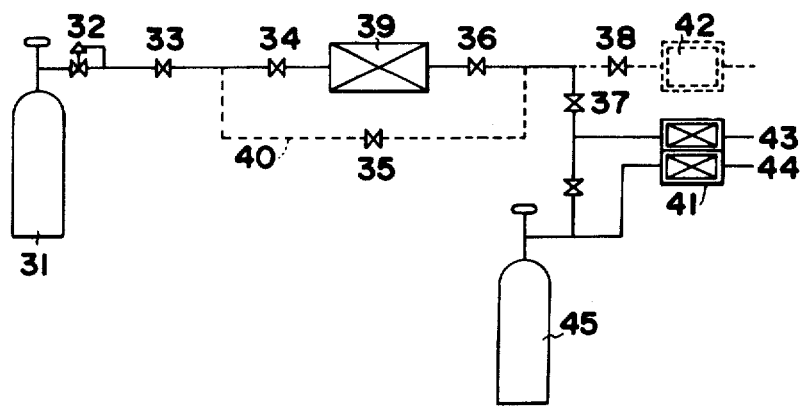
FIG. 4 is a schematic diagram illustrating the series of steps of carrying out this invention.
Figure 5:
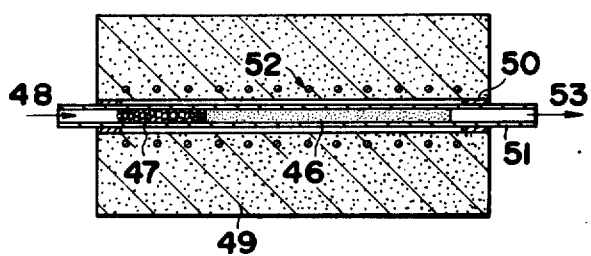
FIG. 5 is a cross-sectional view of an impurity-removing means of FIG. 4.

The method of the present invention can be easily practiced by using the series of steps and the device shown in FIGS. 4 and 5, respectively. FIG. 4 shows the device for carrying out the method of the invention in solid lines, and shows in dotted lines added elements for conducting comparative experiments to show the advantages of the method of the invention.

Referring to FIG. 4, argon gas is introduced through a reducing valve 32, a needle valve 33 and a stop valve 34 into an impurity-removing means 39. The impurities other than hydrogen are removed during the passage through the impurity-removing means 39, and at the outlet thereof the two-component gas mixture consisting of argon and hydrogen is produced.

The thus produced two-component gas is then led through stop valves 36 and 37 to a thermal conductivity detector 41. The detector 41 includes two detecting portions, one of which is for the sample gas and another for a reference gas, i.e. argon carrier gas. The sample gas is introduced into the sample gas detecting portion and is drawn out from and outlet 43 after determination of the thermal conductivity thereof. On the other hand, argon carrier gas is provided from a storage container 45 and introduced into the reference gas detecting portion and is drawn out from an outlet 44 after determining the thermal conductivity thereof.

The hydrogen concentration of the sample argon gas can then be obtained by comparing the thermal conductivity of the sample gas with that of the argon carrier gas.

Referring now to FIG. 5, the impurity-removing means 39 is a quartz column 51, in which the metal getter 46 is packed, in an electric furnace 49 having therein a heat generator 52 for heating the metal getter up to the required temperature and maintaining the high temperature. The circumferential surface of the column 51 is covered by a layer of bricks 50 for preventing radiation of heat.

In the portion of the column 51 near the inlet end 48, there is provided a packing of quartz balls 47 having a diameter of 2 to 3 mm in order to preheat the gas flowing into the column 51.

The sample argon gas is introduced into the column through the inlet 48 through the packing of quartz balls 47, and is preheated during the passage through the quartz balls. The thus preheated sample gas is then passed through the high temperature metal getter portion of the column, and impurities other than hydrogen are removed from the sample gas, and a two-component gas mixture consisting of only argon and hydrogen is drawn out through the outlet 53.

In order to demonstrate how hydrogen concentrations in a sample gas are detected by using the method and apparatus according to the present invention as hereinbefore described, an experiment was conducted using the apparatus of FIGS. 4 and 5. Sample argon gas was artificially prepared by mixing hydrogen, oxygen and nitrogen into argon gas and providing this mixture in a container 31. The impurity removing means 39 was as shown in FIG. 5. Porous titanium particles in an amount of 68 g having a particle size of 14 to 28 mesh and a surface area of 100 to 120 cm²/g (measured by the BET method) were used as the metal getter 46. The getter was heated and maintained at 1000°±15°C in the furnace 49. Sample gas A, which was prepared so as to contain 210 ppm $H_2$, 540 ppm $O_2$, 480 ppm $N_2$, and argon as the remainder, was introduced to the column 51 from the container 31, and was passed through the column at a space velocity of about 4000/H. The hydrogen concentration was continuously measured by the thermal conductivity detector 41.

Another test was then conducted using sample gas B which contained 20 ppm $H_2$, 1250 ppm $O_2$, 5000 ppm $N_2$, and argon as the remainder. The results obtained are shown in the following Table.

In order to judge the accuracy of the measurement according to this invention, a gas chromatograph 42 and a stop valve 38 illustrated by dotted lines in FIG. 4 were used to determine accurate concentrations of hydrogen, oxygen and nitrogen gas, respectively, in the sample gas. The data from the gas chromatograph are also shown in the Table.

A comparative test was conducted for reference, wherein the hydrogen concentration was determined without removing impurities from the sample argon gas. The sample gas flowed through the needle valve 33 and was then led to a by-pass pipe 40 shown by dotted lines in FIG. 4 without passing through the impurity-removing means 39, and was directly introduced through valves 35 and 37 to the thermal conductivity detector 41. The result obtained by the comparative test is also shown in the Table described below.

TABLE

| | PROCESS WITH REMOVAL OF IMPURITIES (PRESENT INVENTION) | | PROCESS WITHOUT REMOVAL OF IMPURITIES (COMPARATIVE TEST) | |
|---|---|---|---|---|
| | INDICATION[1] BY TCD | INDICATION[2] BY GC | INDICATION BY TCD | INDICATION BY GC |
| | SAMPLE GAS A ($H_2$ : 210 ppm; $O_2$ : 540 ppm; $N_2$ : 480 ppm) | | | |
| $H_2$: | 210[3] | 212 | 315 | 210 |
| $O_2$: | — | <1 | — | 545 |
| $N_2$: | — | <1 | — | 485 |
| | SAMPLE GAS B ($H_2$ : 20 ppm; $O_2$ : 1250 ppm; $N_2$ : 5000 ppm) | | | |
| $H_2$: | 20 | 20 | 480 | 20 |
| $O_2$: | — | <1 | — | 1280 |
| $N_2$: | — | <1 | — | 5000 |

[1]Thermal Conductivity Detector
[2]Gas Chromatograph
[3]All Values in the Table are Expressed by ppm by Volume.

As is apparent from the Table, the concentration of a small amount of hydrogen contained in argon can be simply, continuously and accurately determined according to the present invention, even though the argon may contain several impurity gases other than hydrogen.

Comparison of the data for the test in which the impurities were not removed with that obtained by the method of the present invention shows that when the high temperature metal getter is not used, the indication given by the thermal conductivity detector is always larger than the standard indication given by the gas chromatograph, since the sum total of the thermal conductivity values of hydrogen, oxygen and nitrogen is detected, as compared with the thermal conductivity value of only hydrogen mixed with argon in the present invention.

It has thus been shown that the passage of the sample argon gas containing hydrogen through the high temperature metal getter according to the present invention provides the two-component gas mixture consisting of only argon and hydrogen, and the hydrogen concentration in argon can be continuously and accurately determined by directly introducing the two-component gas thus produced into the thermal conductivity detector of the hot-wire bridge type.

In addition, the time which it takes the sample argon gas to be transferred and reach the thermal conductivity detector can be greatly reduced, e.g., to a time of only several seconds, by increasing the linear velocity of the gas passing through the device. On the other hand, although the linear velocity is increased, the impurity-removing function of the metal getter can be easily controlled by adjusting the length of the metal getter packing in the column, because the impurity-removing function depends on the space velocity of the sample argon gas. For this reason, the apparatus according to the present invention can be given a simple design as compared with the prior art apparatus.

Furthermore, the impurity-removing means and the thermal conductivity detector of the present invention can be compactly arranged, and the maintenance of the apparatus can be easily and simply conducted because of the absence of rotatable devices in the apparatus.

It will be understood that the present invention is not to be limited to the details given herein, but that it may be modified within the scope of the appended claims.

What is claimed is:

1. A method for continuously measuring the concentration of hydrogen in argon gas containing hydrogen and other impurities comprising the steps of continuously passing the argon gas containing hydrogen and other impurities through a high temperature metal getter to thereby remove impurities other than hydrogen from the argon gas and produce a two-component gas mixture consisting of argon and hydrogen, continuously detecting the thermal conductivity of the two-component gas mixture, and determining the hydrogen concentration from the thus detected thermal conductivity.

2. The method according to claim 1 wherein said metal getter is a metal selected from the group consisting of titanium, zirconium and niobium.

3. The method according to claim 1 wherein said getter is porous particles of a metal selected from the group consisting of titanium, zirconium and niobium.

4. The method according to claim 1 wherein said metal getter is heated to a temperature of from 900° to 1100°C.

5. An apparatus for measuring the concentration of hydrogen in argon gas containing hydrogen and other impurities comprising an impurity-removing means composed of a high temperature metal getter, means for passing the argon gas through said metal getter, and a thermal conductivity detector coupled to said impurity removing means for detecting the thermal conductivity of the gas passed through the impurity removing means.

6. The apparatus according to claim 5 wherein said impurity-removing means comprises a quartz column in which the metal getter is packed and through which the gas is passed, and means operatively associated with said quartz column for heating the metal getter and maintaining the desired temperature of the getter.

7. The apparatus according to claim 6 wherein said quartz column has therein a packing of quartz balls upstream of the metal getter for pre-heating the gas flowing into the column.

8. The apparatus according to claim 6 wherein said impurity removing means further comprises a layer of bricks surrounding the outer circumference of the quartz column for preventing the radiation of heat.

9. The apparatus according to claim 6 wherein said heating means is an electric furnace.

10. The apparatus according to claim 5 wherein said thermal conductivity detector is a hot-wire bridge type.

11. The apparatus according to claim 5 wherein said metal getter is a metal selected from the group consisting of titanium, zirconium and niobium.

* * * * *